United States Patent
Day et al.

[11] Patent Number: 5,891,157
[45] Date of Patent: Apr. 6, 1999

[54] APPARATUS FOR SURGICAL STEREOTACTIC PROCEDURES

[75] Inventors: James L. Day; Ali Mowlai-Ashtiani, both of Cincinnati, Ohio

[73] Assignee: Ohio Medical Instrument Company, Inc., Cincinnati, Ohio

[21] Appl. No.: 638,616

[22] Filed: Apr. 26, 1996

Related U.S. Application Data

[63] Continuation-in-part of Ser. No. 315,927, Sep. 30, 1994, Pat. No. 5,695,501.

[51] Int. Cl.⁶ .................................................. A61B 19/00
[52] U.S. Cl. ......................... 606/130; 600/417; 600/429
[58] Field of Search ..................... 606/1, 130; 600/417, 600/429

[56] References Cited

U.S. PATENT DOCUMENTS

| | | | |
|---|---|---|---|
| 3,964,480 | 6/1976 | Froning . | |
| 4,341,220 | 7/1982 | Perry . | |
| 4,386,602 | 6/1983 | Sheldon et al. | 606/130 |
| 4,457,300 | 7/1984 | Budde | 606/130 |
| 4,463,758 | 8/1984 | Patil et al. . | |
| 4,475,550 | 10/1984 | Bremer et al. | 606/13 |
| 4,608,977 | 9/1986 | Brown | 606/130 |
| 4,617,925 | 10/1986 | Laitenen | 606/130 |
| 4,618,978 | 10/1986 | Cosman . | |
| 4,706,665 | 11/1987 | Gouda | 606/130 |
| 4,805,615 | 2/1989 | Carol | 606/130 |
| 4,955,891 | 9/1990 | Carol | 606/130 |
| 4,991,579 | 2/1991 | Allen . | |
| 5,006,122 | 4/1991 | Wyatt et al. | 606/130 |
| 5,027,818 | 7/1991 | Bova et al. . | |
| 5,050,608 | 9/1991 | Watanabe et al. . | |
| 5,078,140 | 1/1992 | Kwoh | 606/130 |
| 5,080,662 | 1/1992 | Paul | 606/130 |
| 5,100,411 | 3/1992 | Koutrouvelis . | |
| 5,142,930 | 9/1992 | Allen et al. . | |
| 5,163,430 | 11/1992 | Carol . | |
| 5,186,174 | 2/1993 | Schlondorff et al. . | |
| 5,207,223 | 5/1993 | Adler . | |
| 5,207,688 | 5/1993 | Carol | 606/130 |
| 5,222,499 | 6/1993 | Allen et al. . | |
| 5,230,623 | 7/1993 | Guthrie et al. . | |

(List continued on next page.)

FOREIGN PATENT DOCUMENTS

| | | |
|---|---|---|
| 419070A1 | 3/1991 | European Pat. Off. . |
| 427358 | 5/1991 | European Pat. Off. . |
| 609085 | 8/1994 | European Pat. Off. . |
| 696442A1 | 2/1996 | European Pat. Off. . |
| WO 8809151 | 1/1988 | WIPO . |
| WO 9610368 | 4/1996 | WIPO . |

OTHER PUBLICATIONS

J. Neurosurg 78:138–141, 1993 –"Implantation of intracerebral depth electodes for monitoring seizures using the Pelorus stereotactic system guided by magnetic resonance imaging" by Hwa–Shain Yeh, M.D., Jamal M. Taha, M.D., and William D. Tobler, M.D.

Journal of Computer Assisted Tomography, 17(6):952–960, Nov./Dec. 1993 "Computer–Assisted Coregistration of Multislice SPECT and MR Brain Images by Fixed External Fiducials" by Robert T. Malison, Erik G. Miller, Robin Green, Gregory McCarthy, Dennis S. Charney, and Robert B. Innis.

Advertisement for "CRW Stereotactic System" by Radionics, Inc., 1989.

*Primary Examiner*—Glenn K. Dawson
*Attorney, Agent, or Firm*—Wood, Herron & Evans, L.L.P.

[57] ABSTRACT

A noninvasive apparatus for supporting tools associated with a stereotactic apparatus and procedures to guide tools along any selected path. In one embodiment of the invention, the tool support system is mounted to a skull clamp holding a patient's head. In another embodiment, the tool holder and an articulated arm and probe are mounted to the tool support system which in turn, is mounted to the side rails of a table supporting a patient. With the second embodiment, stereotactic procedures can be practiced with respect to any part of the patient's body.

39 Claims, 3 Drawing Sheets

U.S. PATENT DOCUMENTS

| | | | |
|---|---|---|---|
| 5,257,998 | 11/1993 | Ota et al. | 606/130 |
| 5,263,956 | 11/1993 | Nobles | 606/130 |
| 5,269,305 | 12/1993 | Corol . | |
| 5,279,309 | 1/1994 | Taylor et al. . | |
| 5,284,129 | 2/1994 | Agbodoe et al. | 606/130 |
| 5,300,080 | 4/1994 | Clayman et al. | 606/130 |
| 5,308,352 | 5/1994 | Koutroavelis | 606/130 |
| 5,361,763 | 11/1994 | Kao et al. . | |
| 5,387,220 | 2/1995 | Pisharodi | 606/130 |
| 5,452,720 | 9/1995 | Smith et al. | 606/130 |
| 5,474,564 | 12/1995 | Clayman et al. | 606/130 |
| 5,494,034 | 2/1996 | Schlondorff et al. . | |

APPARATUS FOR SURGICAL STEREOTACTIC PROCEDURES

This application is a continuation-in-part of application Ser. No. 315,927, filed Sep. 30, 1994 for APPARATUS FOR NEUROSURGICAL STEREOTACTIC PROCEDURES, now U.S. Pat. No. 5,695,501.

FIELD OF THE INVENTION

This invention relates to a surgical apparatus generally, and more particularly, to stereotactic systems for use in surgery.

BACKGROUND OF THE INVENTION

During the 1970's radiological imaging systems were developed to assist surgeons in ascertaining the internal condition of a patient in greater detail. Specifically, computer assisted tomography (CAT) systems were developed to enhance images generated from data produced during a radiological scan of a patient. The patient is placed within a gantry, and a radiation source and radiation detectors are positioned opposite one another to be rotated about a portion of the patient's body. The data generated by the radiation detectors are utilized by a computer to generate radiographic images or "slices" of the body position to give a doctor greatly enhanced views through the area of interest.

Later radiographic imaging systems included magnetic resonance (MRI) and positron emission tomography (PET) imaging which generate images from energy sources that do not use x-rays or the like. These devices are useful because they provide different or additional information about organs or tissues than CAT scan images. In this application the term scanners refers to imaging devices regardless of the technique utilized to generate the images.

Surgery may be performed to investigate, repair, or remove anomalies located within the body of a patient. Normally, the only presurgery access to the body available to a surgeon is through images generated by an imaging system. Techniques are known which may be used to identify the location of a lesion or injury within the brain or other portion of the body. In addition, it is often critical to determine a suitable pathway through the brain or body to access that location in order to minimize damage to the intervening tissue. Thus, identifying the pathway to the site may be almost as critical as identifying the site itself, and systems have been developed that are capable of utilizing scanned patient data at a later time and at a different location, for example, in an operating suite.

Such stereotactic systems must first match or co-register the scanned data to the patient. Co-registration is a process by which a computer matches fiducials associated with image data to fiducials associated with the patient's body. The image fiducials are typically selected by using a mouse and cursor to identify on a displayed image points that lie on a patient's skin. An articulated arm and probe are coupled to the computer to provide coordinate data for points external to the computer. Using the arm and probe, the user selects points on the patient that correspond to the selected image fiducials and the computer executes a program that matches the corresponding points. After a sufficient number of points have been selected (usually at least 8), the computer may identify the point in the displayed images that corresponds to the position of the probe proximate the patient's head. Such a system is made by Radionics of Brookline, Mass. and is identified by its product name The Operating Arm.

Such a system provides "navigational" information to a surgeon, that is, the surgeon may bring the probe to a particular location on or within a patient's body and have that location identified on the displayed image. In this way, the surgeon may view areas on the displayed image and determine their proximity to the probe location. In that manner, the surgeon may confirm the surgical approach to a target. Such systems, using an invasive skull ring or a noninvasive probe holder are able to locate, project and display a stabilized image of the surgical path prior to a surgical procedure being performed.

The above systems were initially designed to facilitate intracranial surgery, and therefore, the articulated arm and noninvasive probe holder are coupled to a skull clamp in which the patient's head is mounted. While such a system has proven satisfactory for many neurosurgical procedures, the physical arrangement of equipment has proven to have some limitations. For example, the articulated arm and probe holder extending from one side of the skull clamp provides excellent access to the upper portion of the skull. However, as the area of interest extends toward the lower portions of the skull and upper portions of the spine, the range of orientation of the articulated arm at its more extended positions becomes smaller and limited. Further, with known systems, as the arm of the probe and tool holder is cantilevered from its support; and as it extends out to its longer positions, it becomes less rigid and subject to motion and changes of position from an inadvertent knock or bump.

Therefore, there is a need for a tooling support system that has a greater range of motion, is preferably adjustable, preferably provides transportation for the articulated arm and probe and is very stable regardless of its position and orientation.

SUMMARY OF THE INVENTION

The present invention provides a tooling support system that permits the articulated arm and probe to be moved to any location with respect to the patient.

The present invention provides a tooling support system that provides a very stable platform for stereotactic procedures independent of the position and orientation of the support system.

The present invention provides a tooling support system that permits stereotactic procedures to be performed with respect to any portion of the a patient's body.

In accordance with the principles of the present invention, a support apparatus is connected with respect to a patient support in at least two spaced apart locations. A tool holder is connected to the support apparatus and is adapted to receive a tool at a selectable position with respect to the patient. The tool holder is adjustable to maintain the tool in a selected orientation at the selected position, thereby defining a path between the selected position and a target point within a patient. By connecting the support apparatus in the two spaced apart locations, the tool holder has the advantage of providing a very stable platform from which to perform stereotactic procedures.

In another aspect of the invention, the support apparatus is also adapted to support one end of an articulated arm and probe used in the stereotactic procedures. Further, the support apparatus is laterally supported on side rails of a table supporting the patient. Further, the support apparatus including the articulated arm and probe and tool holder is movable to different locations along the side rails. Therefore, articulated arm and probe and tool holder can be brought into proximity with any part of the patient's body. Therefore, this aspect of the invention has the advantage that the stereotactic apparatus and procedures may be used with respect to any part of the patient's body.

These and other advantages of a system in accordance with the principles of the present invention may be ascertained with reference to the attached drawings and enclosed detailed description.

DETAILED DESCRIPTION OF THE INVENTION

Figure 1:
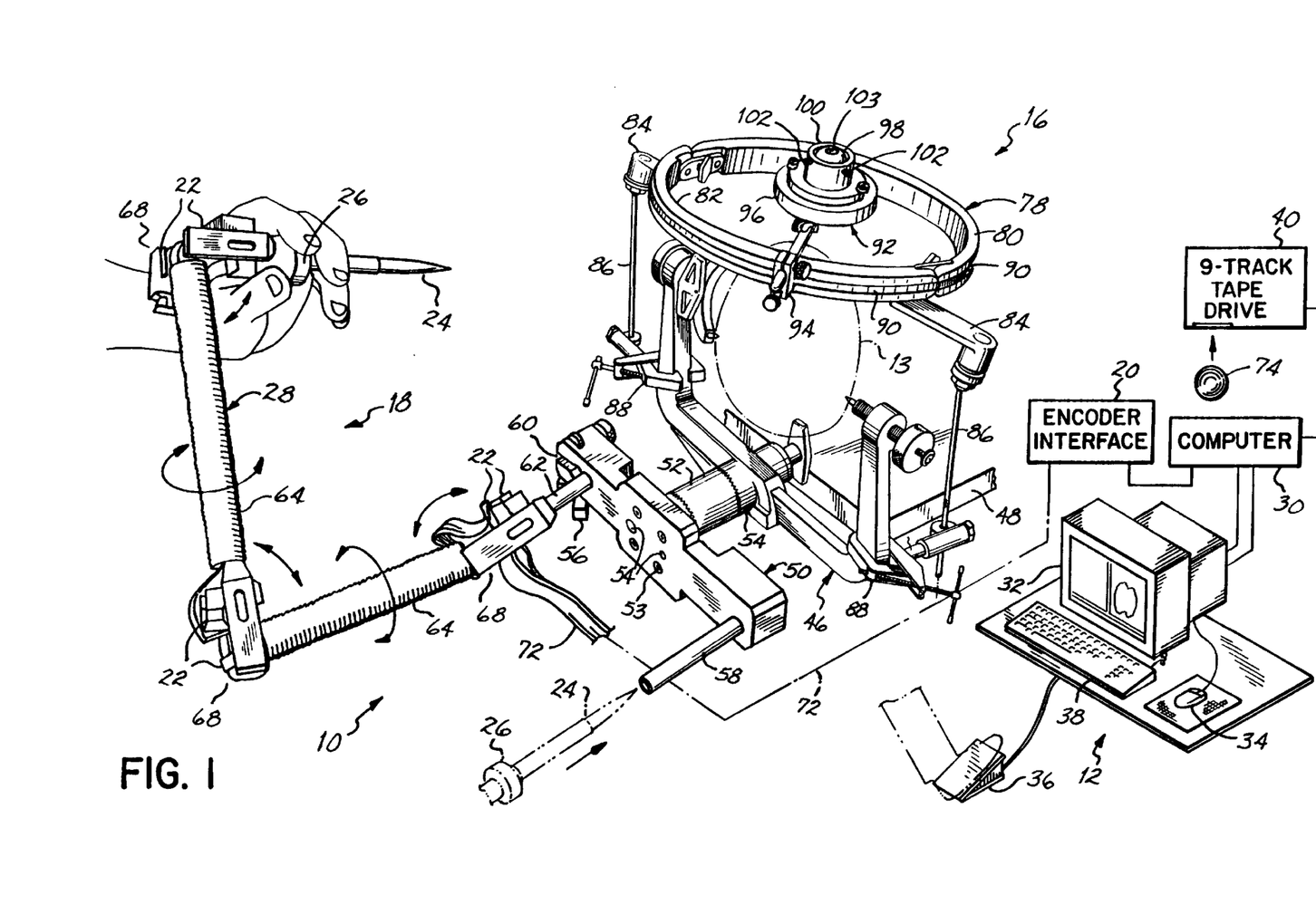
FIG. 1 is a perspective diagrammatic view of the components of one embodiment of a tool support for a stereotactic system in accordance with the principles of the present invention.

A neurosurgical stereotactic system 10 built in accordance with the principles of the present invention is shown in FIG. 1. The system includes an image display subsystem 12, an articulated arm and probe 18, and a tooling support system 16. The image display subsystem 12 displays images from image data generated by a scanner or from data interpolated from such data. Subsystem 12 accepts operator input for selection of fiducials, receives coordinate data from the articulated arm and probe, and co-registers selected fiducials on a patient's head 13 with the selected fiducials for the radiological images for the patient so that the position of the probe and a path to a selected target may be displayed. Subsystem 12 also displays an image of the arm and probe 18 so that the operation of the arm and probe may be verified.

Articulated arm and probe 18 provides spatial data to display subsystem 12 through an encoder interface 20. The spatial data is preferably generated by optical encoders 22, although other spatial coordinate data generating components may be used. Besides the data supplied by the arm and probe 18 used to locate the probe's position, probe finger 24 is rotatably mounted in collar 26 at a distal end of the articulated arm 28 and supplies rotational data with respect to its longitudinal axis. Rotating the probe 24 rotates the displayed image on subsystem 12, as described in more detail below.

Tooling support system 16 stabilizes the probe finger 24 as a surgeon guides it across the patient's head 13. Support system 16 further includes components, discussed in more detail below, that permit the probe finger to be locked into position, and that position utilized to guide surgical instruments to a selected target. Support system 16 further includes components, also discussed in more detail below, that may be used to provide multiple entry points for a surgical path to a target within the patient. These components provide a surgeon with reasonable confidence that each probe finger position provided by the system is directed to the selected target or targets.

Radiological display subsystem 12 includes a computer 30 to which a high resolution graphics monitor 32, a mouse 34, a foot pedal 36, a keyboard 38 and a tape drive 40 are coupled. The computer 12 may additionally include a 3.5 inch diskette drive or the like and a digital audio tape (DAT) drive or the like. The tape drive 40 diskette drive, and DAT drive may be used to provide radiological imaging data to the computer 30. These tape drives may also be used to archive data generated by the computer 30 or to update the software which executes on the computer 30. Computer 30 may also be coupled using conventional techniques to a computer network such as an Ethernet. Such a network may be used to supply radiological image data, software, or diagnostic services.

Preferably, monitor 32 is a Multi-ScanHG Trinitron superfine pitch resolution monitor available from Sony Corporation of America. Preferably, the computer 30 is a Dell 450 DE/2 DGX manufactured by Dell Computers of Houston, Tex. The preferred tape drive 40 for reading image scan data is a 9 track tape drive manufactured by Overland Data of San Diego, Calif. The encoder interface 20 and articulated arm and probe 18 are manufactured by Immersion Human Interface Corp. of San Francisco, Calif.

Preferably, computer 30 executes the "ATLAS" program developed by Nomos Corporation of Pittsburgh, Pa. The "ATLAS" program is a computer program that displays radiological images from radiological scan data supplied by the tapes and interpolates data to provide additional views not present in the radiological scan data. The "ATLAS" program of the preferred embodiment has been modified to accept data from the articulated arm and probe 18 through the encoder interface 20. The program is loaded by using the resident operating system of computer 30 which in the preferred embodiment is the Microsoft Disk Operating System (MS-DOS). The "ATLAS" program includes its own high level I/O routines and other computer resource functions so that the "ATLAS" program uses the primitive level I/O operation of the resident operating system of computer 30. In the preferred embodiment, computer 30 is also provided with a telephone interface so that software and other support functions, such as diagnostics, may be provided via telephone from a remote location.

The articulated arm and probe 18 is mounted to a surgical skull clamp 46 which has been mounted to an operating table 48 (which may be of known type). Base support 50 (FIG. 1) is attached to mounting collars 51, 52 in a known manner using a screw (not shown) that extends centrally through the collars 51, 52 and is threaded into the starburst connector 54 of surgical skull clamp 46. Base support 50 is preferably mounted to collar 51 by Allen screws 53 or the like. Preferably, the mating surfaces of collar 51 and support 50 uses keys 55 so there is only one possible orientation of the base support 50. This feature is important in preserving reference point accuracy when the sterile base support and surgically draped arm are used as discussed in more detail below. Base support 50 also includes a lockable bolt 56 for clamp 60 that secures a mounting shaft 62 at one end of the articulated arm 28. Base support 50 further includes a hollow tubular extension 58 at its second end for holding the probe finger 24.

The articulated arm 28 includes the mounting shaft 62, two arm members 64. Joint members 68 join mounting shaft 62 and arm members 64 to form the articulated arm 28. At each joint, there is rotation in two perpendicular planes to permit two degrees of freedom for each arm. The position of each arm member relative to its respective joint is preferably provided by optical encoders 22 coupled at each joint to the arm in an orthogonal relationship. The rotational movement of probe 24 is used by computer 30 to rotate the radiographic images presented to the surgeon on the screen of monitor 32. Extending from another end of the articulating arm 28 is an interface cable 72 which terminates at an encoder interface 20.

The encoder interface 20 converts the data from the six optical encoders 22 of the articulating arm 28 into rotated position (angular) data for the computer 30.

Tape drive 40 may be used to provide image scan data to the computer 30. Most image scanners archive image data generated from a scan by storing it on magnetic media such as a nine track tape 74. This tape may then be read by a tape drive 40 and supplied to the computer 30 which stores the data on other magnetic media such as a hard disk drive. The image data read from the tape inserted in drive 40 may be used as generated by the scanner. However, each scanner manufacturer may format the data differently. Preferably, the image data generated by the various types of scanners is converted to a standard format prior to being stored on the internal magnetic media of the computer 30. By doing so, the image display program which executes on computer 30 does not require different modules or routines for each format in order to utilize the data from various scanners.

Generally, data generated by a scanner includes image data and non-image data. Non-image data includes definition of parameters such as patient name, date, patient position, scan orientation, scan parameters, and other imaging details peculiar to each of the various scanner manufacturers. The preferred embodiment of the program executing on computer 30 extracts the basic data items common to all of the scanner manufactures and stores them with image data files in a keyword value file. The keyword value file contains a list of key words that identify each data field and the value of that field. For example, a data field identifier for patient name is followed by the data representation of the patient's name for a series scan. These files are preferably human readable for system analysis purposes since they are not usually accessed by a user.

Image data usually includes numerical data that represents a gray scale value or some other brightness/contrast value, such as Hounsfield units, used to generate images, as is well known. These numeric values may be compressed, or expressed as integer or real number values. The preferred embodiment of the program executing on computer 30 uncompresses any compressed values and converts all of the numeric data to integer data. This data is then stored in image data files. These files are preferably written to disk in a hierarchial structure separating the patient data from one another and the image studies and series for each patient.

The foot pedal 36, mouse 34, and keyboard 38 may be used by an operator to provide input to the computer 30. For example, mouse 34 may be used to manipulate a cursor on the screen of monitor 32 to select various options as discussed in more detail below. As a further example, foot pedal 36 may be used by the surgeon to activate the selection of fiducials on a patient.

In the preferred embodiment, the image display program executing in computer 30 includes a graphics user interface (GUI), an input/output (I/0) library, an articulated arm interface program, and a number of application modules. The GUI interface controls the presentation of data and menus on the screen of the monitor 32. The I/O library routines perform various input and output functions such as reading image data from the tape drive 40. The articulated arm interface provides the menu and fiducial selection points displayed at the bottom of the screen on the monitor 32 of the preferred embodiment of the subsystem 12 shown in FIG. 1. Finally, the application modules execute software to perform transform operations to interpolate data for the images and to co-register the image data with the selected patient fiducials, for example.

FIG. 1 illustrates one embodiment of tooling support system 16 that couples the articulated arm and probe 18 to the patient to permit surgical path evaluation and selection. A support apparatus preferably a halo-style annular retractor support 78 commercially available from Ohio Medical Instrument Company of Cincinnati, Ohio includes a movable semi-circular ring section 80 that is pivotally connected to a fixed semi-circular ring section 82. The fixed ring section 82 has support arms 84 that are pivotally mounted on one end of support rods 86. The other end of the support rods 86 are mounted in clamps 88 which, in turn, are mounted to the legs of the skull clamp 46 supporting the patient's head 13. The fixed and movable ring sections 80, 82 have contiguous circumferential paths or slots 90, which preferably are formed as a dovetail channel. Each curvilinear path defines a plane that is substantially nonperpendicular to the patient support.

A tool holder including an alignment ball and socket mount 92 has a block 94 that is mounted in the slots 90 of retractor support 78. The block 94 further supports a ring 96 on which an alignment element preferably an alignment ball 98 and socket 100 are mounted. The alignment ball 98 has a bore 103 shaped to receive the end of the probe 24. Thus, the probe 24 is inserted into the alignment ball 98, and the probe 24 and ball 98 are moved and rotated together with respect to the patient's head 13.

Once a particular orientation has been selected by the surgeon based upon information provided by the radiological image displayed on monitor 32, the screws 102 extending through the socket 100 are tightened to form a clamp that secures the alignment ball 98 in place. A surgical instrument collar of known type (not shown) may then be inserted within the bore 103 of the alignment ball 98 to permit a drill or other instrument 105 (shown in phantom) to be inserted through the instrument collar to open the patient's skull. A biopsy instrument may also be inserted through the collar to the target area. Thus, using the tooling support system 16 illustrated in FIG. 1, stereotactic surgical procedures are performed without the use of an invasive skull ring. In addition, using the known retractor support ring 78, the alignment ball 98 and socket 100 may be located over any desired area of the skull. Further, since the retractor support 78 has two lateral supports, 84, 86, 88, it provides a rigid and stable support for the alignment ball 98 and surgical instruments inserted therethrough, thereby minimizing the potential of the position and/or orientation of the alignment ball 98 changing with respect to the patient's head 13.

Figure 2:
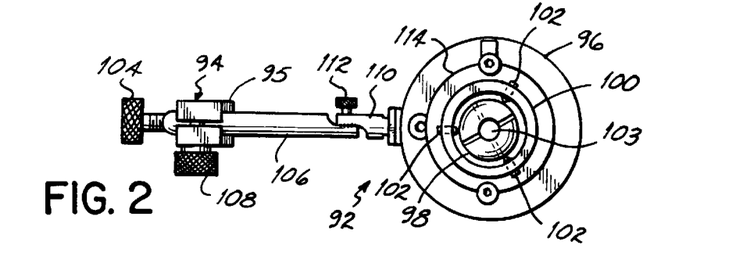
FIG. 2 is a top view of one component of the tool support system illustrated in FIG. 1.

FIG. 2 illustrates the alignment ball and socket mount 92 in further detail. The mounting block 94 has a dovetail 95 shaped to slide within the slots 90. A locking screw 104 clamps the mounting block 94 in a desired circumferential position with respect to the retractor support 78. The mounting block 94 further has a through hole 107 for receiving one end of a first rod 106. The one end of the rod 106 is clamped in the mounting block 94 by locking screw 108. The other end of the rod 106 is connected to one end of rod 110 by locking screw 112 that extends through the end of rod 110 and threadedly engages the other end of rod 106. Therefore, the rod 110 can be rotated with respect to an axis of rotation 109 perpendicular to the rod 106 and subsequently locked into position with the screw 112. The other end of the rod 110 is connected to the ring 96. Preferably, the alignment ball 98 and socket 100 are centrally mounted on a transfer plate 114, which is coupled to the ring 96 in a known manner. Alternatively, the transfer plate 114 and ring 96 may be manufactured as a unitary structure. Further, the mount 92 may be mounted on the retractor support 78 in the position shown in FIG. 1, or it may be inverted to extend below the retractor support 78.

Figures 3, 4:
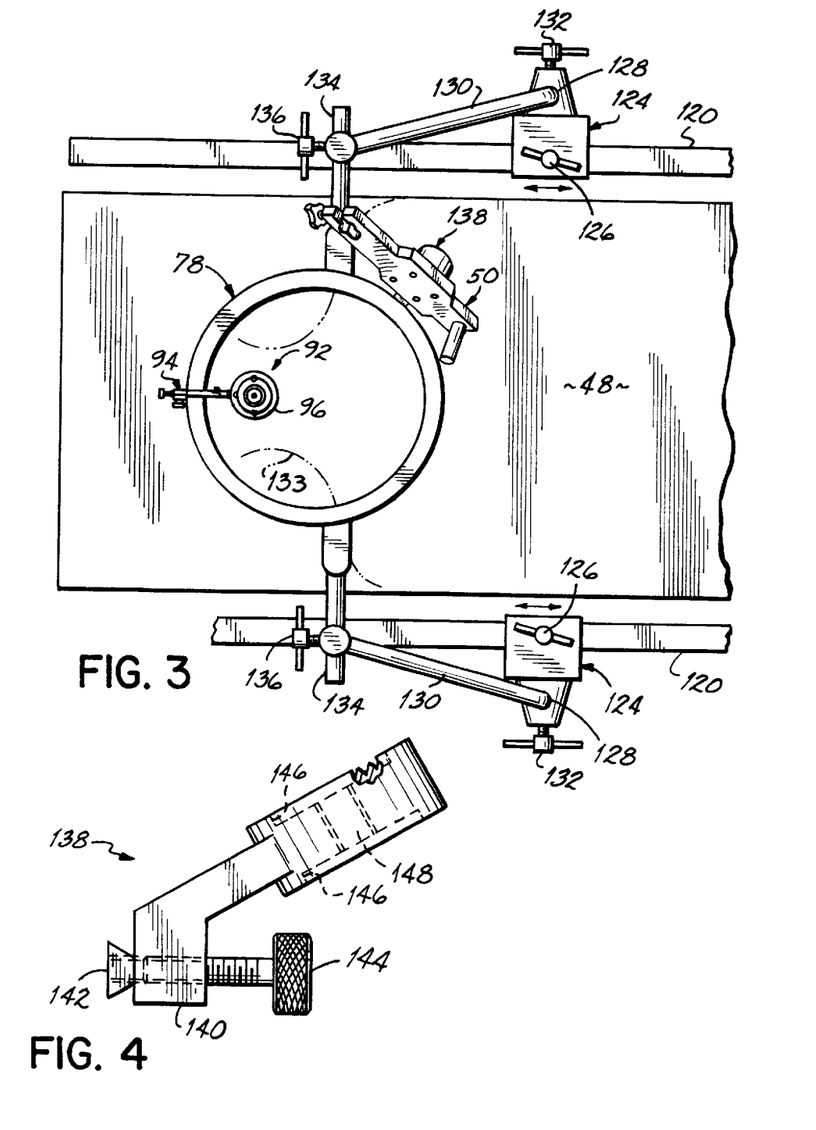
FIG. 3 is a top elevational view of a second embodiment of a tool support for a stereotactic system in accordance with the principles of the present invention.
FIG. 4 is a side view illustrating a bracket for mounting a base support for an articulated arm on a retractor support.

FIG. 3 illustrates another embodiment of the tooling support system 16. In this embodiment, the retractor support 78 is slidably mounted to rails 120 of a table or other patient support 48. Preferably, the rails 120 extend longitudinally along each side of the patient support 48. Side rails fittings 124 commercially available from Ohio Medical Instrument Company, Inc. of Cincinnati, Ohio are adapted to fit over and slide with respect to the slide rails 120. The side rail fittings 124 have respective first locking screws 126 for locking the fitting in a desired location along the side rails. Each of the fittings 124 further has a bore 128 that is formed to slidingly receive a first end of one of the rods 130. Second locking screws 132 are used to secure the rods 130 in a position that places the retractor support 78 at the desired height with respect to the patient 133 as shown in phantom. The other ends of the rods 130 are slidingly mounted over arms 134 extending laterally from the retractor support 78. Locking screws 136 are used to secure the retractor support 78 in the desired side-to-side position with respect to the patient. The embodiment of the tooling support system 16 illustrated in FIG. 3 permits the retractor support 78 to be positioned at any desired location with respect to the patient. However, to provide the capability of performing the stereotactic procedures heretofore described, it is also necessary to provide transportation for the articulated arm and probe 18 (FIG. 1).

Referring to FIG. 4, an articulated arm base support bracket 138 has a mounting block 140 with a dovetail projection 142 at one end that is shaped to slide within the slots 90 of the retractor support 78. A locking screw 144 is used to secure the base support bracket 138 in the desired circumferential position on the retractor support 78. The mounting block 140 has, at its other end, opposing connecting elements with a threaded, centrally located through-hole 148. Each of the connecting elements 146 has a starburst or toothed ring that is shaped to mate with the toothed ring on the end of the collar 52 (FIG. 1) that connects to the skull clamp 46. It should be noted that the base support bracket 38 can be mounted in the position illustrated in FIG. 4, or in an inverted position in which the counter-bores 146 extend above the dovetail projection 142. The collar 51 is inserted in the desired counter-bore 146, and a centrally located screw (not shown) extends from the distal end of the collar 51 and into the threaded hole 148, thereby securing the collar 51 to the retractor support 78. Thereafter, the base support 50 is attached to the collar 52 with the screws 53 shown in FIG. 1. With the apparatus illustrated in FIG. 3, the articulated arm and probe assembly 18 is movable with the retractor support 78 to any desired longitudinal position with respect to the patient. Therefore, stereotactic procedures can be performed at any body location around the skull, down the spine or in the areas of the patient's legs. Consequently, the stereotactic procedures can be used with respect to any portion of the patient's anatomy.

The tooling support system 16 of FIG. 3 is especially useful for utilizing stereotactic procedures in spinal surgery. One such surgical procedure to connect the C-1 and C-2 vertebrae. In that procedure, screws are inserted in the transarticular area of the two vertebrae. Such screws are also known as transarticular or PARS screws. That procedure utilizes a tool holder such as a screw alignment frame 150, which is illustrated in detail in FIG. 5. The screw alignment frame 150 has a mounting block 152 with a dovetail 154 shaped to engage and slide within the slots 90 of the retractor support 78. A locking screw 156 is used to secure the alignment frame 150 in the desired circumferential position on the retractor support 78. One end of a first support rod 159 extends through a bore within the mounting block 152. A locking screw 158 is used to secure the first rod 159 within the mounting block 152. One end of a second support rod 160 is coupled to the other end of the first support rod 159. The adjoining ends of the support rods 159, 160 are held together by a locking screw 162, and the support rods 159, 160 can be adjusted to have different angular positions with respect to each other. The other end of the second rod 160 is connected to an aligning device 164.

Figure 5:
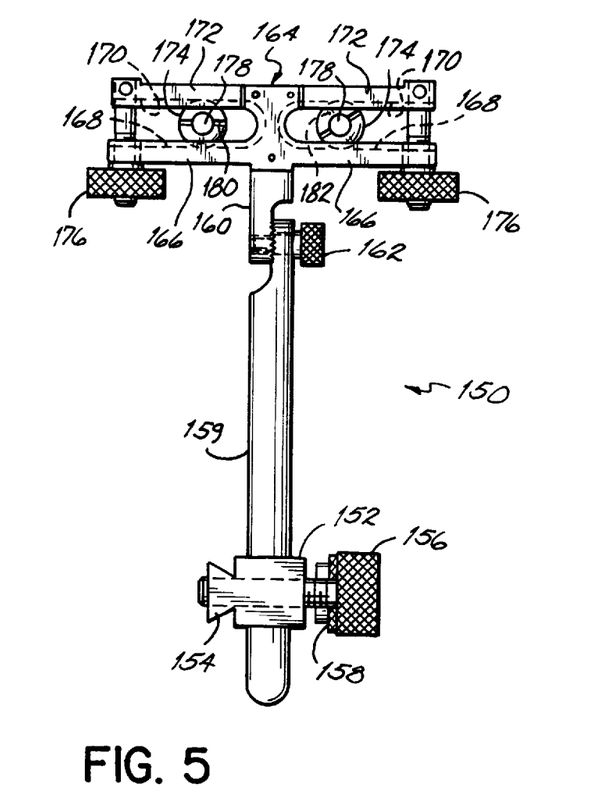
FIG. 5 is an elevational view illustrating a screw positioning frame for a stereotactic system in accordance with the principles of the present invention.

The aligning device 164 has fixed arms 166 that contain respective grooves 168 that are contiguous with mating grooves 170 that are located in movable arms 172 that have one end hinged to pivot with respect to the fixed arms 166. Alignment balls 174 are disposed within the grooves 168, 170. The grooves may be arcuate in cross-section, V-shaped, or have any other profile that helps to maintain the balls 174 between the arms 166, 172. When the locking screws 176 are loosened, the alignment balls are free to move along the grooves 168, 170, as well as swivel to different orientations within the grooves. The alignment balls 174 have respective centrally located bores 178, which are sized to receive the probe 24 (FIG. 1). Each of the balls 174 further has a first slot 180 that extends from one end of the bore 178 diametrically across the ball and extends from an opposite end of the bore 178 longitudinally along a substantial portion of the bore 178. Each of the balls has a second slot 182, which is generally perpendicular to the first slot 180, extends diametrically across the alignment ball and longitudinally over a substantial length of the bore 178.

In use, the positioning frame 150 is mounted within the retractor support 78. The positioning frame 150 and retractor support 78 are then generally positioned such that the alignment frame is approximately at its desired position with respect to the C1 and C2 vertebrae. After the articulated arm and probe 18 have been intialized using the alignment sleeve 58 (FIG. 1), the probe is inserted into the center bore 178 of one of the alignment balls 174. Using the scanned data and the known stereotactic apparatus as previously generally described, the probe 24, and the one of the alignment balls 174 is further manipulated until the probe is pointing in a desired direction through the transarticular area of the two vertebrae. That desired direction represents the desired path for one of the screws. When the desired path is identified, a locking screw 176 associated with the one of the alignment balls containing the probe 24 is tightened until the one of the alignment balls is locked in its desired position and orientation. The probe is then removed and inserted in the other of the alignment balls 174. The positioning and alignment process is repeated until the probe is oriented in a direction such that its longitudinal axis is collinear with the desired path of the second screw; and the locking screw 178 associated with the other alignment ball 174 containing the probe 24 is tightened to secure the alignment ball 174 in its desired position and orientation.

Thereafter, known guides (not shown) are inserted through the center bores 178 of the alignment balls 174, and the adjustment screws 176 are tightened further to hold the guides firmly within their respective alignment balls 174. A first drill is inserted through one of the guides, and the desired hole for one of the screws is drilled through the two vertebrae. The drill is maintained in its position within the alignment ball and both vertebrae while a second drill is used with the other of the guides to drill a second hole through the two vertebrae. Therefore, the positioning device 150 used in combination with known stereotactic procedures permits the desired paths for the screws to be precisely determined with respect to the fractured vertebrae. Further, after drilling the first hole, by maintaining the drill bit in position, the two vertebrae are securely held in position while the second hole is being drilled. With the positioning frame 150, the screws can be held in their precise desired alignment throughout the entire procedure repairing the fractured vertebrae.

While the present invention has been illustrated by the description of an alternative embodiment, and while the embodiments have been described in considerable detail, it is not the intention to restrict or in anyway limit the scope of the appended claims to such detail. Additional advantages and modifications will readily appear to those skilled in the art. The invention in its broadest aspects is therefore not limited to the specific details, representative image system and illustrative examples shown and described. Accordingly, departures may be made from such details without departing from the spirit or scope of applicant's general inventive concept.

What is claimed is:

1. A tooling support apparatus for use with a stereotactic apparatus being used to perform a procedure on a patient supported by a patient support comprising:
   a support apparatus providing a path of motion in a plane;
   a rod having a lower end adapted to be connected to the patient support and having an upper end connected to the support apparatus, the rod holding the support apparatus at a desired elevation above the patient support; and
   a tool holder including
      a support element mounted to the support apparatus and movable along the path of motion to selected positions with respect to the support apparatus and the patient,
      a first alignment element rotatably mounted on the support element and adapted to receive a tool, the first alignment element being selectively rotatable to change the orientation of the first alignment element without changing its position with respect to the patient, thereby defining a surgical path between the tool and a target point within the patient, and
      a first clamp operably mounted with respect to the first alignment element for selectively locking the first alignment element at a desired orientation.

2. The tooling support apparatus of claim 1 wherein the upper end of the rod is pivotally connected to the support apparatus.

3. The tooling support apparatus of claim 1 wherein the rod is adapted to be connected with respect to the patient support at selectable points along a length of the rod.

4. The tooling support apparatus of claim 1 wherein the patient support includes a skull clamp and the rod is adapted to be mounted to the skull clamp.

5. The tooling support apparatus of claim 4 wherein the rod is adapted to be connected to the skull clamp at selectable points along a length of the rod.

6. The tooling support apparatus of claim 1 wherein the patient support includes a table and the rod is adapted to be mounted with respect to the table.

7. The tooling support apparatus of claim 6 wherein the table includes a side rail and the rod is adapted to be mounted with respect to the side rail.

8. The tooling support apparatus of claim 1 further comprising a bracket having one end mounted with respect to the support apparatus and an opposite end adapted to receive a probe tip on one end of an articulated arm.

9. The tooling support apparatus of claim 8 wherein the path of the support apparatus is a dovetail path and the one end of the bracket has a dovetail sized to slide in the dovetail path of the support apparatus.

10. The tooling support apparatus of claim 9 wherein the opposite end of the bracket has a connecting element adapted to receive a connecting element of a support base connected to one end of the articulated arm.

11. The tooling support apparatus of claim 1 wherein the support element of the tool holder further comprises:
    a first shaft having one end adjustably coupled to the support apparatus; and
    a second shaft having one end rotatably connected and selectively lockable to an opposite end of the first shaft to permit the second shaft to be oriented at an angle with respect to the first shaft, whereby the tool holder is selectively moved to a desired position by adjusting the positions of the first and second shafts.

12. The tooling support apparatus of claim 11 wherein the support element further comprises a member mounted to the support apparatus and having a bore for rotationally receiving the one end of the first shaft to permit a selected length of the first shaft to extend through the clamp at a selectable angle.

13. The tooling support apparatus of claim 1 further comprising a second rod connected at an upper end to the support apparatus and a lower end of the second rod is adapted to be connected to the patient support, the rods holding the support apparatus at the desired elevation above the patient support.

14. The tooling support apparatus of claim 13 wherein the patient support includes a table having a side rail extending longitudinally along each side of the table and one of the support rods is adapted to be mounted to one of the side rails.

15. The tooling support apparatus of claim 14 wherein one of the rods is adapted to be selectively movable to different locations along the side rails.

16. The tooling support apparatus of claim 13 wherein the tool holder further comprises:
    a bracket having one end mating with and connectable to the curvilinear member, the bracket extending from the curvilinear member to a location inside the circumference of the curvilinear member and being movable and lockable with respect to the curvilinear member at a selected position with respect to the patient.

17. The tooling support apparatus of claim 16 wherein the support apparatus has a dovetail path and the one end of the bracket has a dovetail sized to slide in the dovetail path of the support apparatus.

18. The tooling support apparatus of claim 16 wherein the tool holder further comprises:
    a second alignment element rotatably mounted on the support element and adapted to receive a tool; and
    a second clamp disposed with respect to the second alignment element for locking the second alignment element in a selected orientation.

19. The tooling support apparatus of claim 18 wherein the first and second clamps include respective first and second paths for receiving the first and second alignment elements, respectively, thereby permitting each of the alignment elements to change position with respect to each other.

20. The tooling support apparatus of claim 19 wherein the first and second alignment elements are generally spherical in shape and have a bore extending diametrically therethrough.

21. The tooling support apparatus of claim 20 wherein the first and second alignment elements rotate within their respective first and second paths.

22. The tooling support apparatus of claim 1 wherein the support apparatus is a curvilinear member and the path of motion extends around a circumference of the curvilinear member.

23. The tooling support apparatus of claim 22 wherein the path of motion is a a circular path.

24. The tooling support apparatus of claim 23 wherein the circular path is a dovetail channel.

25. The tooling support apparatus of claim 1 wherein the first alignment element is generally spherical in shape with a bore extending diametrically therethrough.

26. A tooling support apparatus for use with a stereotactic apparatus being used to perform a procedure on a patient supported by a patient support comprising:
   a support apparatus adapted to be connected with respect to the patient support; and
   a tool holder including
      a support element mounted to the support apparatus and movable to selected positions with respect to the patient,
      first and second alignment elements rotatably mounted on the support element and adapted to simultaneously receive tools, each of the first and second alignment elements being independently movable to selectively change position and orientation of its respective tool with respect to the patient, thereby defining two surgical paths extending into the patient from the two tools.

27. A tooling support apparatus of claim 26 wherein the support element of the tool holder further comprises:
   a first shaft having one end adjustably coupled to the support apparatus; and
   a second shaft having one end rotatably connected and selectively lockable to an opposite end of the first shaft to permit the second shaft to be oriented at an angle with respect to the first shaft, the first and second alignment elements being rotatably mounted with respect to the second shaft, whereby the first and second alignment elements are selectively moved to respective desired positions by adjusting the positions of the first and second shafts.

28. The tooling support apparatus of claim 26 wherein the tool holder further comprises a clamp mounted with respect to the alignment elements for locking the alignment elements in selected orientations.

29. The tooling support apparatus of claim 28 wherein the tool holder comprises first and second clamps disposed with respect to the first and second alignment elements, respectively, for locking the alignment elements in selected positions.

30. The tooling support apparatus of claim 29 wherein the first and second clamps include respective first and second paths for receiving the first and second alignment elements, respectively, thereby permitting each of the alignment elements to change position with respect to each other.

31. The tooling support apparatus of claim 30 wherein the first and second alignment elements are generally spherical in shape and have a bore extending diametrically therethrough.

32. The tooling support apparatus of claim 31 wherein the first and second alignment elements rotate within their respective first and second paths.

33. A tooling support apparatus of claim 30 wherein the support element of the tool holder further comprises:
   a first shaft having one end adjustably coupled to the support apparatus; and
   a second shaft having one end rotatably connected and selectively lockable to an opposite end of the first shaft to permit the second shaft to be oriented at an angle with respect to the first shaft, the first and second alignment elements being rotatably mounted with respect to the second shaft, whereby the first and second alignment elements are selectively moved to respective desired positions by adjusting the positions of the first and second shafts.

34. A tooling support apparatus of claim 33 wherein the second shaft pivots with respect to the first shaft about an axis of rotation substantially perpendicular to a length of the first shaft, and the first and second alignment elements move in the respective first and second paths in a direction substantially parallel to the axis of rotation.

35. A tooling support for use with a stereotactic system being used to perform a procedure on a patient supported by a patient support comprising:
   a support apparatus;
   a rod having a lower end adapted to be connected to the patient support and having an upper end connected to the support apparatus, the rod holding the support apparatus above the patient support; and
   a tool holder including
      a support element mounted on the support apparatus and being movable to and lockable at selected positions relative to the support apparatus above the patient support,
      a generally spherical alignment element rotatably mounted on the support element and adapted to receive a tool, the alignment element being pivotable with respect to the tool holder to selectively change the orientation of the alignment element without changing its position with respect to the patient, thereby defining a surgical path between the tool and a target point within the patient, and
      a clamp operably mounted with respect to the alignment element for selectively locking the alignment element at a desired orientation.

36. A tooling support for use with a stereotactic system being used to perform a procedure on a patient supported by a patient support comprising:
   a support apparatus providing a path of motion in a plane;
   a rod having a lower end adapted to be connected to the patient support and having an upper end connected to the support apparatus, the rod holding the support apparatus such that the plane of motion is at a desired elevation above the patient support; and
   a tool holder mounted on the support apparatus and adapted to receive a tool, the tool holder including
      a first shaft having one end adjustably coupled to the support apparatus,
      a second shaft having one end rotatably connected and selectively lockable to an opposite end of the first shaft to permit the second shaft to be oriented at an angle with respect to the first shaft,
      an alignment element rotatably mounted at an opposite end of the second shaft and adapted to receive a tool at the desired position with respect to the patient, the alignment element being selectively adjustable to change the position and orientation of the tool to define a path between a target point within the patient, and
      a clamp operably mounted with respect to the alignment element for selectively locking the alignment element.

37. The tooling support of claim 36 wherein the tool holder further comprises a member mounted to the support apparatus and having a bore for rotationally receiving the one end of the first shaft to permit a selected length of the first shaft to extend through the clamp at a selectable angle.

38. The tooling support of claim 37 wherein the support apparatus includes a curvilinear member having a path extending around a circumference of the curvilinear member.

39. A tooling support for use with a stereotactic system being used to perform a procedure on a patient supported by a patient support comprising:

a support apparatus providing a path of motion in a plane:

a rod having a lower end adapted to be connected to the patient support and having an upper end connected to the support apparatus, the rod holding the support apparatus such that the plane of the path of motion is substantially nonperpendicular to and above the patient support; and     a tool holder including         a support element mounted on the support apparatus and being movable to and lockable at selected positions along the path of motion relative to the support apparatus,         a generally spherical alignment element rotatably mounted on the support element and adapted to receive a tool, the alignment element being selectively pivotable with respect to the patient to define a surgical path between the tool and a target point within the patient, and         a clamp operably connected to the alignment element for selectively locking the alignment element with respect to the support element.

\* \* \* \* \*